United States Patent [19]
Cutrer

[11] Patent Number: 5,997,463
[45] Date of Patent: Dec. 7, 1999

[54] LASER WELDED BRACHYTHERAPY SOURCE AND METHOD OF MAKING THE SAME

[75] Inventor: L. Michael Cutrer, North Hollywood, Calif.

[73] Assignee: North American Scientific, Chatsworth, Calif.

[21] Appl. No.: 09/048,517

[22] Filed: Mar. 26, 1998

[51] Int. Cl.$^6$ .............................. A61M 36/00; A61N 5/00
[52] U.S. Cl. .................................................. 600/8; 29/592
[58] Field of Search ............................. 600/1–8; 29/592; 228/60, 101

[56] References Cited

U.S. PATENT DOCUMENTS

| | | |
|---|---|---|
| 1,718,899 | 6/1929 | Fischer . |
| 1,954,868 | 4/1934 | Failla et al. ................................. 600/8 |
| 3,351,049 | 11/1967 | Lawrence . |
| 3,663,685 | 5/1972 | Evans . |
| 4,101,646 | 7/1978 | Sugimoto . |
| 4,323,055 | 4/1982 | Kubiatowicz . |
| 4,675,150 | 6/1987 | Russell, Jr. et al. . |
| 4,702,228 | 10/1987 | Russell, Jr. et al. . |
| 4,784,116 | 11/1988 | Russell, Jr. et al. . |
| 4,827,493 | 5/1989 | Parsons et al. . |
| 4,874,613 | 10/1989 | Hsiao . |
| 4,891,165 | 1/1990 | Suthanthiran . |
| 5,080,278 | 1/1992 | Streckenbach et al. . |
| 5,084,002 | 1/1992 | Liprie . |
| 5,163,896 | 11/1992 | Suthanthiran et al. . |
| 5,405,309 | 4/1995 | Carden, Jr. . |
| 5,460,592 | 10/1995 | Langton et al. . |
| 5,503,614 | 4/1996 | Liprie .......................................... 600/7 |
| 5,575,749 | 11/1996 | Liprie . |
| 5,683,345 | 11/1997 | Waksman et al. . |

OTHER PUBLICATIONS

"I–125 Seed Source Model 6702" leaflet.

Primary Examiner—Samuel Gilbert
Attorney, Agent, or Firm—Pillsbury Madison & Sutro LLP

[57] ABSTRACT

A brachytherapy source for use in radiation treatment of the body includes radioactive material, and a housing. The housing is used to contain the radioactive materials, and is formed by at least one tube having two ends. The two ends of the at least one tube are sealed by welding such that a radiation distribution of the brachytherapy source approximates a point source that is free of cold zones to minimize underexposure or overexposure of the body to radiation and to simplify the placement of the brachytherapy source in the body. Preferably, the ends of the at least one tube are sealed by laser welding, and a laser performs the laser welding while the brachytherapy source is rotated relative to the laser, which is activated in short pulses. For example, the laser is activated in a first series of pulses to initially collapse one end of the at least one tube and to at least partially close off the one end, then the laser is activated for a second series of pulses to seal off the one end of the at least one tube and remove excess material, next the laser is activated in a third series of pulses to initially collapse the other end of the at least one tube and to at least partially close off the other end, and finally, the laser is activated for a fourth series of pulses to seal off the other end of the at least one tube and remove excess material.

31 Claims, 4 Drawing Sheets

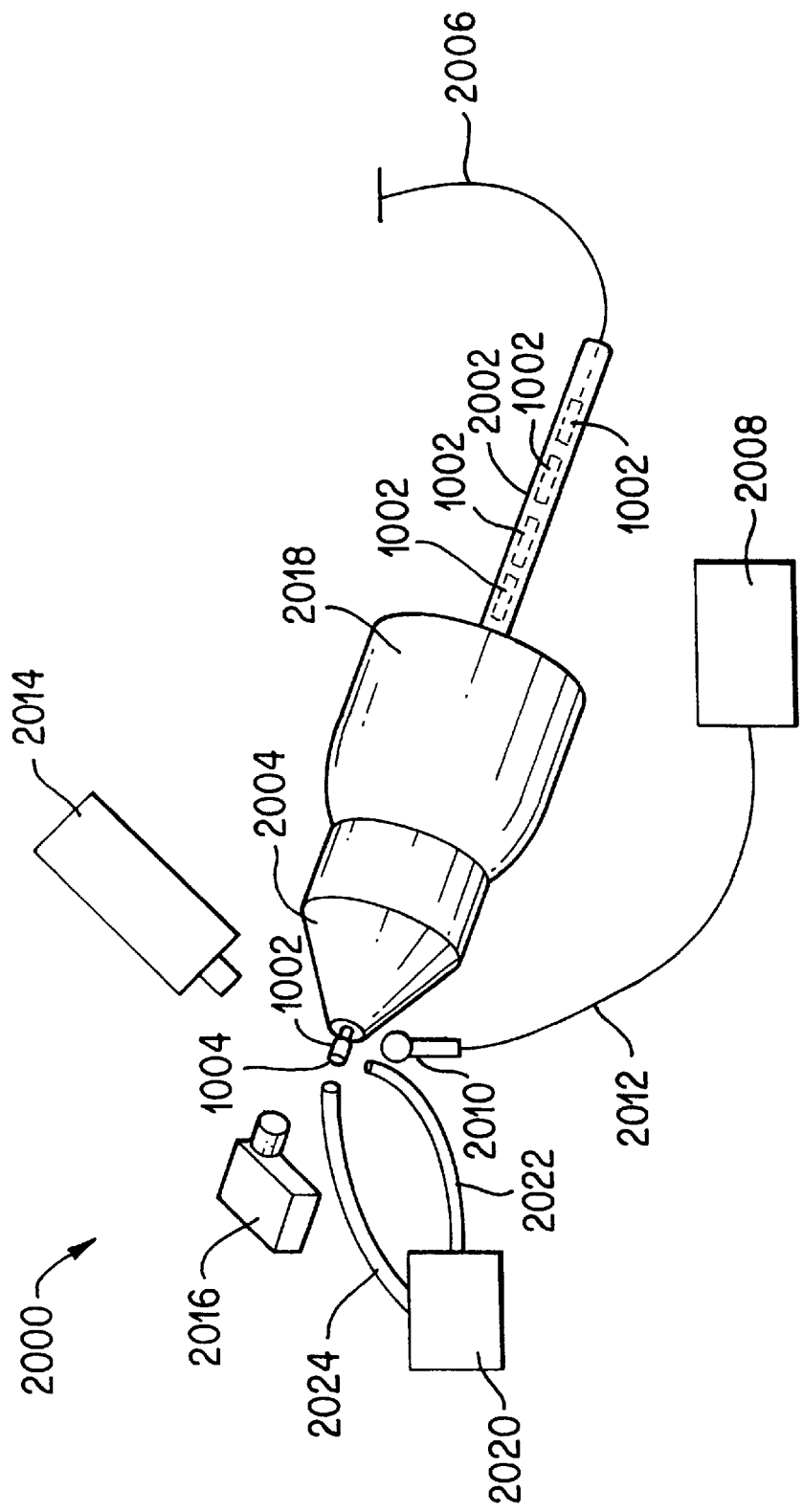

LASER WELDED BRACHYTHERAPY SOURCE AND METHOD OF MAKING THE SAME

FIELD OF THE INVENTION

This invention relates to laser welding methods and, in particular embodiments, to a laser welded brachytherapy source and a method of laser welding the brachytherapy source.

BACKGROUND OF THE INVENTION

Over the years, brachytherapy sources implanted into the human body have become a very effective tool in radiation therapy for treating diseased tissues, especially cancerous tissues. The brachytherapy sources are also known as radioactive seeds in the industry. Typically, these brachytherapy sources are inserted directly into the tissues to be irradiated using surgical methods or minimally invasive techniques such as hypodermic needles. These brachytherapy sources generally contain a radioactive material such as iodine-125 which emits low energy X-rays to irradiate and destroy malignant tissues without causing excessive damage to the surrounding healthy tissue, as disclosed by Lawrence in U.S. Pat. No. 3,351,049 ('049 patent). Because radioactive materials like iodine-125 have a short half-life and emit low energy X-rays, the brachytherapy sources can be left in human tissue indefinitely without the need for surgical removal. However, although brachytherapy sources do not have to be removed from the embedded tissues, it is necessary to permanently seal the brachytherapy sources so that the radioactive materials cannot escape into the body. In addition, the brachytherapy source must be designed to permit easy determination of the position and the number of brachytherapy sources implanted in a patient's tissue to effectively treat the patient. This information is also useful in computing the radiation dosage distribution in the tissue being treated so that effective treatment can be administered and to avoid cold spots (areas where there is reduced radiation).

Many different types of brachytherapy sources have been used to treat cancer and various types of tumors in human or animal bodies. Traditional brachytherapy sources are contained in small metal capsules, made of titanium or stainless steel, are welded or use adhesives, to seal in the radioactive material.

These various methods of permanently sealing the brachytherapy sources, used so that the radioactive materials cannot escape into the body and do not have to be removed after treatment, can have a dramatic effect on the manufacturing costs and on the radiation distribution of the brachytherapy sources. Increased costs reduce the economic effectiveness of a brachytherapy source treatment over more conventional procedures such as surgery or radiation beam therapy. In addition, the poorer radiation distribution effects, due to these sealing methods, in conventional brachytherapy sources may ultimately affect the health of the patient, since higher doses of radiation are required or additional brachytherapy sources must be placed inside the human body. All which leads to a less effective treatment that can damage more healthy tissue than would otherwise be necessary.

A first type of conventional brachytherapy source 10 is shown in FIG. 1, and uses two metal sleeves 12 and 14. The brachytherapy source 10 is disclosed in U.S. Pat. No. 4,891,165 issued Jun. 2, 1990 to Sutheranthiran and assigned to Best Industries of Springfield Va. Each of the sleeves has one closed end 16 and 18 using die-drawn techniques. Sleeve 14 has an outer diameter that is smaller than an inner diameter of the sleeve 12 to permit the sleeve 14 to slide inside sleeve 12 until the open end of sleeve 14 contacts the closed end 16 of the sleeve 12. Radioactive material, such as pellets, are placed inside the smaller sleeve 14, and then the larger external sleeve 12 is slid over the smaller sleeve 14. Next, the brachytherapy source 10 is permanently sealed by TIG (Tungsten Inert Gas) welding the open end of the larger sleeve 12 to the closed end 18 of the smaller sleeve 14. Laser welding may also be used. Although the welding of the two sleeves 12 and 14 together provides a good seal, the brachytherapy source 10 suffers from several drawbacks.

One drawback results from the radiation seed 10 being formed from two distinctly different sized pieces (the two sleeves 12 and 14), which involves an additional assembly step of fitting the two sleeves 12 and 14 together. This is time consuming and can slow the assembly process down, as well as increase the overall cost of producing the brachytherapy sources 10.

Another conventional brachytherapy source 30, as shown in FIG. 2, uses a single tube 32 which has end caps 34 and 36 inserted at the ends 38 and 40 of the single tube 32 to hold the radioactive material. The brachytherapy source 30 is disclosed in U.S. Pat. No. 4,784,116 issued Nov. 15, 1988 to Russell, Jr. et al. and assigned to Theragenics Corporation of Atlanta, Ga. The ends 38 and 40 are then welded, or adhesively secured, to the end caps 34 and 36 to close off and seal the brachytherapy source 30. Although the brachytherapy source 10 provides a single wall and a better radiation distribution along the length (or sides) of the brachytherapy source 30, the brachytherapy source 30 still suffers from several drawbacks.

A first drawback is that the ends 38 and 40 of the brachytherapy source 30 do not provide a uniform radiation distribution approximating a point source, because the end caps 34 and 36 provide a double wall at the end of the brachytherapy source 30 that blocks off a substantial amount of radiation. A further drawback results form the welds used to seal the end caps 34 and 36 to the ends 38 and 40 of the singe tube 32, since these also reduce the radiation distribution. Another drawback results from there being a three-step assembly process; rather, than the two step assembly process discussed above, since there are now three separate parts to be assembled together (the single tube 32 and the end caps 34 and 36).

In an alternative to this type of conventional brachytherapy source, a brachytherapy source 50, as shown in FIG. 3, has end plugs 52 and 54 that are slid into the open ends of a single tube 56. The brachytherapy source 50 is disclosed in U.S. Pat. No. 5,683,345 issued Nov. 4, 1997 to Waksman et al. and assigned to Novoste Corporation of Norcross, Ga. The end plugs 52 and 54 are either secured in place with an adhesive and the metal of the single tube 56 is then bent around the end plugs 52 and 54, or the end plugs 52 and 54 are welded to the single tube 56. The brachytherapy source 50 suffers from the same drawbacks as discussed above. In addition, the radiation distribution out the end plugs 52 and 54 is substantially reduced due to the added thickness of the end plugs 52 and 54.

In another conventional brachytherapy source 70, as shown in FIG. 4, some of the drawbacks of the multiple piece assembly are overcome by using a single tube 72 to provide a body with a uniform side wall along the length of the brachytherapy source 70. The brachytherapy source 70 is distributed by Amersham International PLC. One end 74 of the single tube 72 is TIG welded, and then the radioactive material is inserted into the open end 76 of the single tube 72. Next the open end 76 is TIG welded to seal the single tube 72 to provide a single unitary brachytherapy source structure. However, the brachytherapy source 70 suffers from many drawbacks.

For example, TIG welding the ends 74 and 76 causes formation of a bead of molten metal at the ends 74 and 76 of the single tube 72. Due to the nature of TIG welding the welded ends 74 and 76 generally form a bead that may be as thick as the diameter of the single tube 72. Therefore, the radiation distribution is substantially diminished out of the ends 74 and 76 of the brachytherapy source 72 due to the thickness of the beads 78 and 80 closing off the ends 74 and 76. In addition, the end 76 is only closed after the radioactive material is inserted into the single tube 72, and the end 76 may not seal in the same manner due to the presence of the radioactive material carrier body effecting the thermal characteristics of the brachytherapy source 70. Thus, the bead 80 can be a different shape than the bead 78, which may further alter the radiation distribution and could lead to inconsistent radiation distributions from one brachytherapy source to another, making the prediction of the actual radiation distribution more difficult.

Therefore, although the brachytherapy source 70 overcome some of the drawbacks in the earlier brachytherapy sources by minimizing the assembly steps associated with multiple pieces, it does not provide an even radiation distribution. In fact, due to the potential for variations of the second end during the TIG welding, the distribution can vary substantially from brachytherapy source 70 to brachytherapy source 70. Typical radiation distribution patterns for conventional brachytherapy sources 70 using the single tube 72 are shown in FIGS. 5(a) and 5(b). As is shown in FIGS. 5(a) and 5(b), the radiation distribution patterns 102 and 104 tend to diminish substantially toward the ends 74 and 76 of the brachytherapy source 70 and form cold zones 106 and radiation lobes 108. This means that depending on how the brachytherapy sources 70 are placed adjoining each other, there may be cold spots in the radiation distribution between adjoining brachytherapy sources 70, where cells are not receiving radiation from the cold zones 106 at the ends 74 and 76. Or if the adjoining brachytherapy sources are placed close enough together, to assure no cold spots from the presence of the cold zones 106, there will be overlapping areas in the radiation lobes 108 that may provide an excessive dose of radiation. Either of these two conditions could result in either too much or too little radiation, which results in a less effective medical treatment.

SUMMARY OF THE DISCLOSURE

It is an object of an embodiment of the present invention to provide an improved brachytherapy source and method of making the same, which obviates for practical purposes, the above mentioned limitations.

According to an embodiment of the invention, a brachytherapy source for use in radiation treatment of the body includes radioactive material, and a housing. The housing is used to contain the radioactive materials, and is formed by at least one tube having two ends. In preferred embodiments, the two ends of the at least one tube are sealed by welding such that a radiation distribution of the brachytherapy source approximates a spherical shape of a theoretical point source that is substantially free of cold zones to minimize underexposure or overexposure of the body to radiation and to simplify the placement of the brachytherapy source in the body.

Preferably, the ends of the at least one tube are sealed by laser welding, and a laser performs the laser welding while the brachytherapy source is rotated relative to the laser. In addition, the laser is activated in short pulses. For example, the laser is activated in a first series of pulses to initially collapse one end of the at least one tube and to at least partially close off the one end of the at least one tube, then the laser is activated for a second series of pulses to seal off the one end of the at least one tube and remove excess material, next the laser is activated in a third series of pulses to initially collapse the other end of the at least one tube and to at least partially close the one off end of the at least one single tube, and finally, the laser is activated for a fourth series of pulses to seal off the other end of the at least one tube and remove excess material. In preferred embodiments, each of the two sealed ends taper from a thickness of a wall of the at least one tube to a predetermined maximum thickness to minimize the effect on the radiation distribution and to substantially prevent the formation of cold zones. In particular embodiments, the thickness of the wall of the at least one tube is equal to or less than 0.002 inches, and wherein the predetermined maximum thickness is less than or equal to 0.030 inches.

In particular embodiments of the present invention, the radioactive material is selected from a group consisting of iodine-125 and palladium-103. Also, the radioactive material is formed as spherical beads. The brachytherapy source may also include a marker material that is contained in the housing to identify the position of the brachytherapy source in the body. In particular embodiments, the marker material is formed as at least two separate markers to indicate orientation as well as position of the brachytherapy source.

In further embodiments, a method of manufacturing a brachytherapy source for use in radiation treatment of the body includes the steps of providing a radioactive material and forming a housing. The housing is formed from at least one tube having two ends to contain the radioactive material. Next, the two ends of the at least one tube are welded to seal the radioactive material in the at least one tube such that a radiation distribution of the brachytherapy source approximates a point source that is free of cold zones to minimize underexposure or overexposure of the body to radiation and to simplify placement of the brachytherapy source in the body. In further embodiments, the ends of the at least one tube are welded by laser welding, and the laser welding is performed by rotation of the brachytherapy source relative to a laser that is activated in short pulses.

Particular embodiments of the laser welding method include the steps of: activating the laser in a first series of pulses to initially collapse one end of the at least one tube and to at least partially close off the one end of the at least one single tube; activating the laser for a second series of pulses to seal off the one end of the at least one tube and to remove excess material; activating the laser in a third series of pulses to initially collapse the other end of the at least one tube and to at least partially close of the other end of the at least one tube; and activating the laser for a fourth series of pulses to seal off the other end of the at least one tube and to remove excess material.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 8 is a generalized system schematic of a laser welding apparatus in accordance with an embodiment of the present invention.

DETAILED DESCRIPTION OF THE PREFERRED EMBODIMENTS

Figure 1:
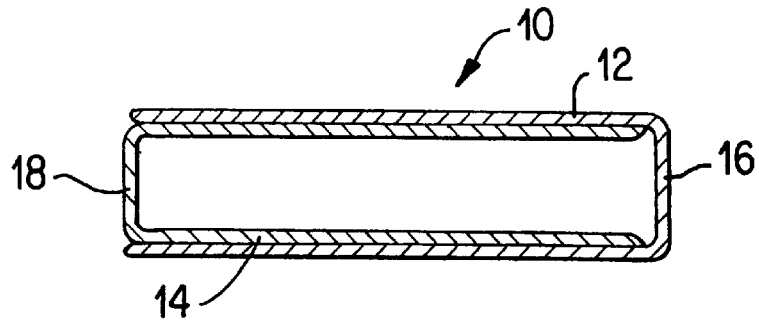
FIG. 1 is a cross-sectional view of a first type of conventional brachytherapy source.
Figure 2:
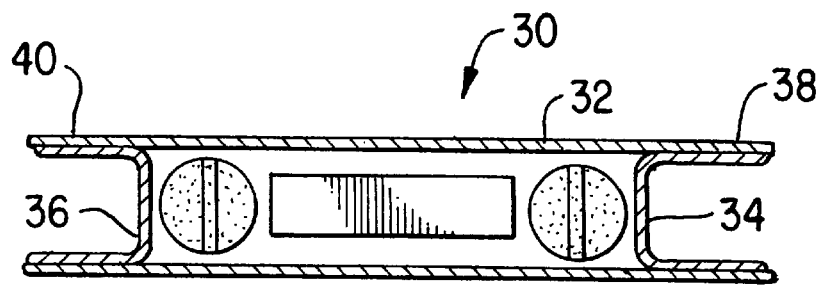
FIG. 2 is a cross-sectional view of a second type of conventional brachytherapy source.
Figure 3:
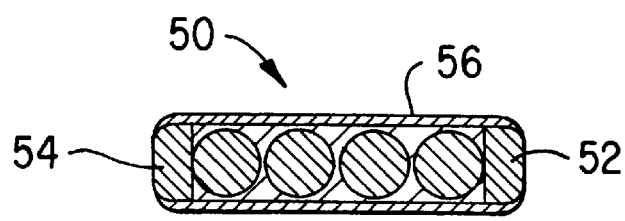
FIG. 3 is a cross-sectional view of a third type of conventional brachytherapy source.

As shown in the drawings for purposes of illustration, the invention is embodied in an improved brachytherapy source with a more even radiation distribution and a method of making the same. In preferred embodiments of the present invention, the brachytherapy sources are for use in the treatment of cancer in humans and animals. However, it will be recognized that further embodiments of the invention may be used in other small radiation sources, such as those used for identification or the like, in which consistent and even radiation distributions are required, or may be used to treat other illnesses, such as heart disease, pain, non-cancerous growths, gland therapy or the like. Other embodiments of the present invention may be utilized to weld other small capsules requiring tight tolerances on the sealed end of the capsules.

Figure 6:
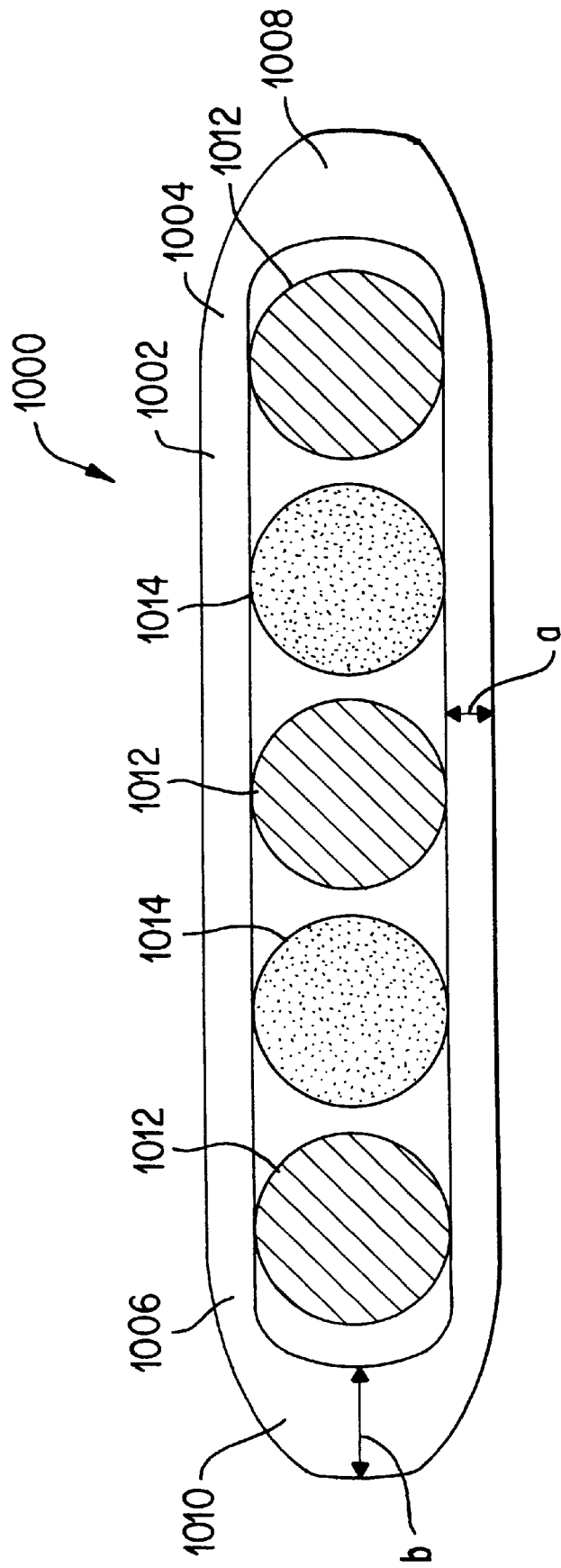
FIG. 6 is a cross-sectional view of a brachytherapy source in accordance with an embodiment of the present invention.

As shown in FIG. 6, a brachytherapy source 1000 in accordance with an embodiment of the present invention utilizes a unitary capsule formed with laser welding technology. The laser welding procedure provides for consistency of the welds in the brachytherapy sources to enable the production of radiation sources that are consistent in characteristics from one brachytherapy source to another. Preferably, the brachytherapy source 1000 uses a single tube 1002 having two ends 1004 and 1006 that are sealed by welds 1008 and 1010. The single tube 1002 contains the radioactive material 10012 and the marker material 1014. The single tube 1002 of the brachytherapy source 1000 may be formed from titanium, stainless steel, nickel, metal, or any other material, suitable for welding and which meets medical application criteria. The single tube 1002 is selected to have an initial wall thickness of 0.002 inches, as shown at "a" in FIG. 6. In alternative embodiments, the single tube 1002 thickness may be thinner or thicker, with the thickness being determined by the material contained in the seed, the radiation distribution pattern desired, the strength of the radiation desired, and the environment in which the brachytherapy source 1000 will be used. Although a single tube 1002 is preferred, alternative embodiments may use multiple tubes that are joined together, so long as an even radiation distribution around the brachytherapy source can be obtained.

In preferred embodiments, once the ends 1004 and 1006 have been sealed by the welds 1008 and 1010, the welds 1008 and 1010 taper from the wall thickness of 0.002 inches (shown as "a" in FIG. 6) to a maximum thickness of 0.020 inches (shown as "b" in FIG. 6) at the point 1016. However, the maximum thickness of 0.020 inches only occurs at the extreme end of the brachytherapy source 1000 and tends to taper off substantially to the 0.002 thickness as the welds 1008 and 1010 merge with the wall of the single tube 1002. The tapered welds 1008 and 1010 avoid the thick bead that forms across a single tube when conventional TIG welding is used in the earlier embodiments. In alternative embodiments, different wall thicknesses may be used, with the thickness being dependent on the type of radioactive material being used, the size of the brachytherapy source, and the material used to form the single tube 1002, such that wall thickness may range from 0.001 inches to 0.010 inches or higher, and the maximum weld thickness may range from 0.002 inches to 0.030 inches or higher.

Figure 5A:
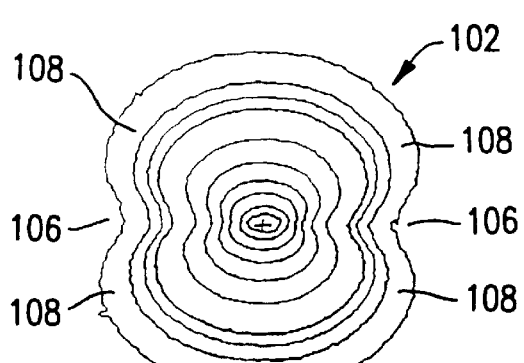
FIGS. 5(a) and 5(b) are radiation distribution diagrams for the conventional brachytherapy source shown in FIG. 4.
Figure 7A:
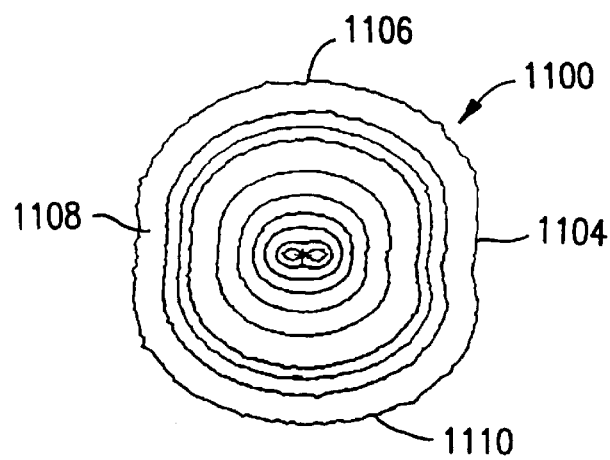
FIGS. 7(a) and 7(b) are radiation distribution diagrams for the embodiment of the brachytherapy source shown in FIG. 6.
Figure 5B:
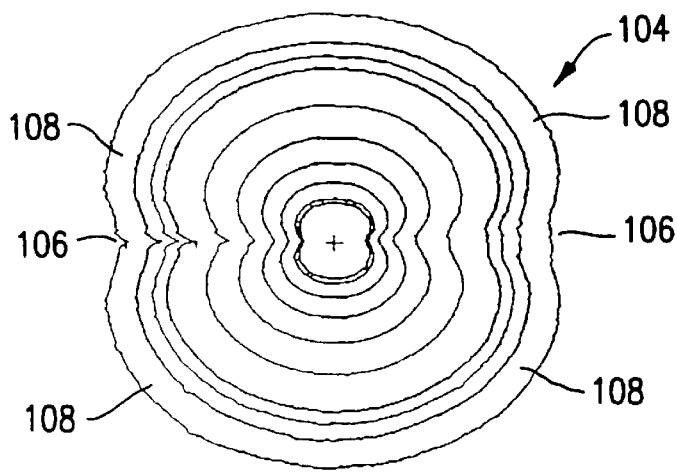
Figure 7B:
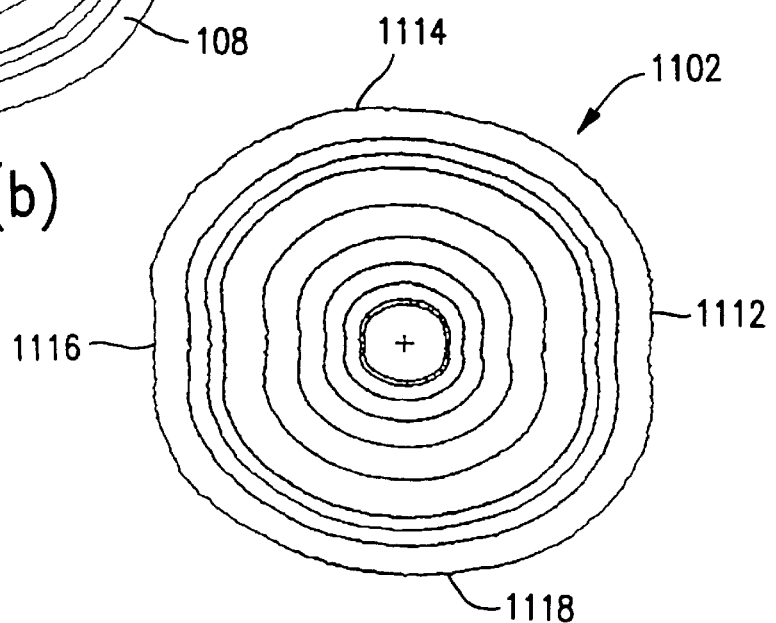

The result of the laser welding procedure is a brachytherapy source 1000 that provides a very even and consistent radiation distribution with only a minimal dip (or cold zone) through the ends 1004 and 1006, as shown by the radiation distributions in FIGS. 7(a) and 7(a), as compared to those produced in brachytherapy sources that are formed using conventional TIG welding or plug closures, as shown in FIGS. 5(a) and 5(b). As shown in FIGS. 7(a) and 7(b), the radiation distributions 1100 and 1102 are substantially uniform between sides 1104, 1106, 1108, 1110, 1112, 1114, 1116 and 1118, regardless of direction. Thus, the brachytherapy source 1000 has been shown to provide a good approximation of a theoretical, spherical radiation point source. The preferred brachytherapy sources are linear elements, and tend to produce a more ovoid radiation source, than the theoretical spherical point source. However, as shown in FIGS. 7(a) and 7(b), the radiation distribution approximates a theoretical, spherical point source when observed from a distance of as little as 1 cm. In further embodiments, it may be possible to adjust the length of the brachytherapy source, the thickness of the single tube 1002, the placement of radioactive materials 1012 in the single tube 1002, and maximum thickness of the laser welds 1008 and 1010 to approximate theoretical point sources at observable distances that are substantially less than 1 cm.

The preferred radiation material 1012 is iodine-125 or palladium-103. However, in alternative embodiments, other radioactive materials, such as cobalt-57, cobalt-60, cesium-137, iridium-192, or the like may be used. Preferably, the marker material 1014 is made of gold or sliver. However, in alternative embodiments, the marker material may be formed out of other radiation blocking materials, such as lead or the like. In preferred embodiments the radiation material 1012 and the marker material 1014 are spherical. In addition, multiple markers 1014 can be used, as shown and described in U.S. patent application Ser. No. 08/904,695 filed Aug. 1, 1997, which is herein incorporated by reference, to indicate position as well as orientation of the brachytherapy source 1000.

In particular embodiments, the interior of the brachytherapy source 1000 at the welds 1008 and 1010 are curved to further minimize the thickness and radiation attenuation at the thickest part of the welds 1008 and 1010. This interior curvature is the result of the welding process, which first collapses the ends 1004 and 1006 of the singe tube 1002 and then quickly liquefies the collapsed ends 1004 and 1006 to form the welds 1008 and 1010 sealing the brachytherapy source 1000. In further embodiments, the interior curvature can be accentuated by using spherical radioactive material 1012 or marker material 1014 in the ends 1004 and 1006 of the brachytherapy source. This assists in distributing the heat and minimizes formation of a bead as the softened (or slightly melted) ends 1004 and 1006 conform to the shape of the radioactive material to produce a curved interior surface that minimizes the thickness of the welds 1008 and 1010.

The brachytherapy sources 1000 are manufactured using precisely controlled laser welding techniques. As shown in FIG. 8, a laser welding system 2000 includes a series of single tubes 1002 having ends 1004 and 1006 contained in a guide tube 2002. The guide tube 2002 is used to feed the single tubes 1002 to a chuck 2004, which holds and rotates the single tube 1002 during the laser welding process. The single tubes 1002 are moved through the guide tube 2002 towards the chuck 2004 by a push wire 2006. In preferred embodiments, the push wire is moved incrementally by a step motor assembly (not shown); however, in alternative embodiments, the push wire may be advanced manually or by other automated advancing techniques. In alternative embodiments, the guide tube 2002 and/or the push wire 2006 may be omitted and the single tubes may be delivered to the chuck 2004 by other methods known in the art.

Once the single tubes 1002 are fed into the chuck 2004, a Geiger counter 2008 connected to a radiation sensor 2010 through a cable 2012 determines if any of the radioactive material 1012 is positioned under the laser 2014. If radioactive material 1012 is detected, the laser welding procedure for that brachytherapy source 1000 is aborted to avoid radiation contamination from exposure and vaporization of the radioactive material 1012 by the laser 2014. If no radioactive material 1012 is detected, the laser welding procedure will continue. In addition, a video camera 2016 is used to line up the ends 1004 and 1006 of the single tube 1002 to assure accurate placement of the laser welds 1008 and 1010. In further embodiments, a stop (not shown) may be positioned to stop the progression of the single tube 1002 as it is fed through the chuck 2004. When the single tube 1002 is position, the chuck 2004 is engaged and the stop is removed prior to the welding.

In preferred embodiments, one end of the single tube 1002 is crimped, and then the radioactive material (and any marker material) are loaded into the single tube 1002 (e.g., by vacuum suction through the crimped end or by sliding the radioactive material (and any marker material) in through the open end and then pushing it into position against the crimped end of the single tube 1002. In alternative embodiments, one end of the single tube 1002 is laser welded first and then radioactive material (and any marker material) are loaded into the single tube prior to laser welding the other end of the single tube 1002. Alternatively, one end may be crimped, next the radioactive material (and any marker material) are loaded into the open end of the single tube 1002, and finally the other end is crimped prior to laser welding the brachytherapy source 1000. In further alternatives, a temporary filler compound is placed inside each open end 1004 and 1006 of the single tube 1002, which is then cut off during the laser welding procedure. In an alternative embodiment, rather than crimping the single tube 1002, one end of the single tube 1002 may be sealed by laser welding prior to insertion of the radioactive material (and any marker material). To facilitate good thermal characteristics of this weld, a wire may be positioned inside of the single tube 1002 to simulate the presence of radioactive material (and any marker material). Then the wire is removed and the radioactive material (and any marker material) are inserted into the open end of the brachytherapy source after which the open end of the brachytherapy source is laser welded in the manner described above.

Prior to activating the laser 2014, the chuck 2004 is rotated at high speed relative to the laser 2014 by a drive motor 2018 connected to the chuck 2004. This allows the laser 2014 to apply a laser welding beam on all sides of the single tube 1002. Rotation assists in preventing too much heat from being generated on one side of the single tube 1002, and thereby over liquefy or collapse unevenly. In addition, the relatively minor centrifugal forces generated on the single tube 1002, helps minimize the collapse of the single tube 1002. In preferred embodiments, the chuck 2004 rotates at 42 RPM; however, in alternative embodiments higher or lower RPMs, for example, RPMs in the range of as low as 10 RPM or as high as 100 RPM (or even substantially higher with proper control of the laser) may be used, with the RPMs being selected based on the diameter of the single tube 1002, the thickness of the single tube 1002, and the type of material used to form the single tube 1002. In further alternative embodiments, the laser may be rotated around a stationary chuck and single tube to produce the laser welded ends.

In preferred embodiments, the single tube 1002 has a first end 1004 laser welded, then the single tube 1002 is replaced by another single tube 1002 supplied by the guide tube 2002. After all of the single tubes 1002 have had the end 1004 laser welded to form the weld 1008, the single tubes 1002 are turned around and reloaded into the guide tube 2002 to seal the other end 1006 of the single tubes 1002 with the laser weld 1010. As discussed above, radioactive material (and any marker material) may be loaded before or in between the laser welding of the ends 1004 and 1006 of the single tube 1002. In alternative embodiments, the end 1004 of the single tube is sealed with the laser weld 1008, and then the other end 1006 is immediately laser welded with the weld 1010 before moving onto another single tube 1002.

In preferred embodiments, an inert gas source 2020 supplies inert gas, such as helium, argon or the like, through outlet hose 2022 across the exposed single tube 1002 during laser welding of the ends 1004 and 1006. The presence of the inert gas minimizes or eliminates oxidation during the laser welding procedure. In addition, the inert gas can be used to quickly cool the end 1004 and 1006, and the laser welds 1008 and 1010, of the single tube 1002 to more accurately control formation of the welds 1008 and 1010. An optional suction tube 2024 is used to remove the inert gas and recycle the inert gas for use in later laser welds.

Figure 4:
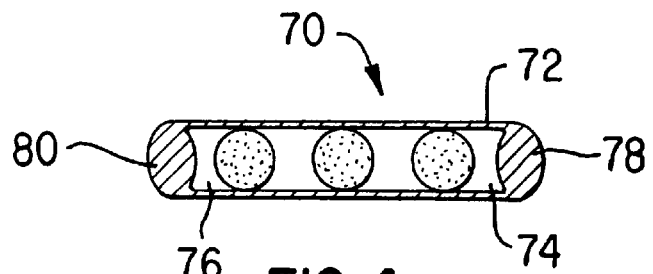
FIG. 4 is a cross-sectional view of a fourth type of conventional brachytherapy source.

To achieve the desired laser welds 1008 and 1010, very careful control of the laser welding procedure must be used to avoid forming a large bead at the end of the brachytherapy source, which would distort the radiation distribution to resemble the pattern for the brachytherapy source 70, as shown in FIGS. 4, 5(*a*) and 5(*b*). Preferably, for each weld 1008 and 1010, two separate pulse periods from the laser 2014 are used. The first series of pulses by the laser consists of 30 pulses at the rate of 8 pulses a second and 226 V from the laser 2014, which is primarily directed at least partially closing off the end of the single tube 1002. Thus, the first set of pulses by the laser 2014 melts (or softens) the metal so that it starts to collapse and form a bead, but the laser 2014 is then stopped to permit the metal of the single tube 1002 to cool. A second series of pulses by the laser consists of 30 pulses at the rate of 8 pulses a second and 244 V. The second series of pulses cuts off excess material from the ends 1004 and 1006, and remelts the ends of the partially closed single tube 1002 to seal off the ends 1004 and 1006 and form the welds 1008 and 1010. The higher voltage in the second series of pulses assists in removing the excess material. In alternative embodiments, a single series of pulses may be used to from the welds 1008 and 1010; however, experience has shown that it is more difficult to accurately control the formation of the welds 1008 and 1010. The two pulse series makes obtaining the desired welds 1008 and 1010 easier to obtain. In addition, rather than varying voltage between the two series of pulses, the number of pulses may be varied. Also, different voltage levels may be used as long as excessive melting does not occur, which would then form a bead on the end of the single tube 1002; rather than the consistent welds obtained by carefully controlling voltage, number of pulses, and the timing of the pulses.

In preferred embodiments, a laser of 10 watts from Unitek Miyachi Corp, of Monrovia, Calif. is used, however, smaller or larger lasers may be used. In preferred embodiments, a high powered laser source is used since it quickly melts and congeals the metal to avoid a thickening or beading effect similar to what is encountered in TIG welding procedures. In alternative embodiments, an electron beam, or the like, may be used instead of a laser. However, electron beams are not preferred, since they require a complete vacuum in the welding environment, whereas laser welding may be performed in the presence of a stream of inert gases at normal air pressure. In still further alternative embodiments, it may be possible to adapt TIG welding methods to provide a more controlled weld that approximates that obtainable by the Laser welding procedure. This might be done by limiting the heat distribution, timing and possibly drawing out the ends rather than folding them over, as is done in conventional TIG welding.

A key aspect to controlling the formation of the welds 1008 and 1010, on the ends 1004 and 1006 of the single tube 1002 of the brachytherapy source 1000, is to control the heat distribution and the amount of energy applied to the ends 1004 and 1006 of the single tube 1002. This is controlled by setting rotation rate, laser power levels, laser pulse length, the number of laser pulses, the number of; laser pulse series, and the amount of inert gas applied for a particular type of single tube 1002. Thus, one can use higher or lower rotation rates by adjusting the other factors, such as, for example, the laser pulse length or the number of laser pulses. The important aspect of the laser welding procedure is to control the rate and the amount of the melting experienced by the ends 1004 and 1006 of the single tube 1002 during the laser welding procedure. Insufficient heat fails to seal the brachytherapy source 1000, and too much heat forms a large bead and results in a brachytherapy source that is similar to the brachytherapy source 70, as described above.

In preferred embodiments, the single tube 1002 has a circular cross-section. However, in alternative embodiments the single tube 1002 may utilize different tube cross-sections, such as square, rectangular, triangular, hexagonal, or the like, may be used.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A brachytherapy source for use in radiation treatment of an affected tissue region, the brachytherapy source comprising:

radioactive material; and a housing for containing the radioactive material, the housing being formed by at least one tube having an axis and two ends, the at least one tube having a maximum exterior diameter transverse to the axis, wherein the two ends of the at least one tube are sealed to form a tapering of each end from the maximum exterior diameter which permits a radiation distribution of the brachytherapy source which approximates a spherical point source that is substantially free of cold zones.

2. A brachytherapy source according claim 1, wherein the radioactive material is selected from a group consisting of iodine-125 and palladium-103.

3. A brachytherapy source according to claim 1, wherein the radioactive material is formed as spherical beads.

4. A brachytherapy source according to claim 3, further including a marker material, wherein the marker material is also contained in the housing to identify the position of the brachytherapy source in the body.

5. A brachytherapy source according to claim 4, wherein the marker material is formed as at least two separate markers to indicate orientation as well as position of the brachytherapy source.

6. A brachytherapy source according to claim 1, wherein at least one of the ends of the tube includes a laser welded seal.

7. A brachytherapy source according to claim 6, wherein the laser welded seal is formed by a rotation of the brachytherapy source relative to a source of laser radiation.

8. A brachytherapy source according to claim 7, wherein the laser welded seal is formed in response to short pulses from the source of laser radiation at the ends of the at least one tube.

9. A brachytherapy source according to claim 8, wherein the laser welded seal is formed in response to a first series of pulses of laser radiation to initially collapse one end of the at least one tube and to at least partially close off the one end of the single tube, and a second series of pulses of laser radiation to seal off the one end of the at least one tube and remove excess material.

10. A brachytherapy source according to claim 1, wherein each of the two sealed ends taper from a thickness of a wall of the at least one tube to a predetermined maximum thickness to minimize the effect on the radiation distribution and to substantially prevent the formation of cold zones.

11. A brachytherapy source according to claim 10, wherein the thickness of the wall of the at least one tube is equal to or less than 0.002 inches, and wherein the predetermined maximum thickness is less than or equal to 0.030 inches.

12. A method of manufacturing a brachytherapy source for use in radiation treatment of an affected tissue region, the method comprising the steps of:

providing radioactive material;

forming a housing from at least one tube having two ends to contain the radioactive material, the at least one tube having an axis and a maximum exterior diameter transverse to the axis: and welding the two ends of the at least one tube to seal the radioactive material in the at least one tube to form a tapering of each end from the maximum exterior diameter such that a radiation distribution of the brachytherapy source approximates a spherical point source that is substantially free of cold zones.

13. A method according claim 12, further comprising the step of selecting the radioactive material contained in the housing from a group consisting of iodine-125 and palladium-103.

14. A method according to claim 12, further comprising the step of forming the radioactive material into spherical beads.

15. A method according to claim 14, further including the step of providing marker material, and placing the marker material in the housing to identify the position of the brachytherapy source in the body.

16. A method according to claim 15, further comprising the step of forming the marker material as at least two separate markers to indicate orientation as well as position of the brachytherapy source.

17. A method according to claim 12, wherein the step of welding comprises welding the ends of the at least one tube by laser welding.

18. A method according to claim 17, wherein a laser performs the laser welding, the method further comprising the step of performing the laser welding by rotation of the brachytherapy source relative to the laser.

19. A method according to claim 18, further comprising the step of activating the laser in short pulses to laser weld the ends of the at least one tube.

20. A method according to claim 19, further comprising the steps of:
   activating the laser in a first series of pulses to initially collapse one end of the at least one tube and to at least partially close off the one end;
   activating the laser for a second series of pulses to seal off the one end of the at least one tube and remove excess material;
   activating the laser in a third series of pulses to initially collapse the other end of the at least one tube and to at least partially close off the other end; and
   activating the laser for a fourth series of pulses to seal off the other end of the at least one tube and remove excess material.

21. A method according to claim 12, further comprising the step of tapering each of the two sealed ends from a thickness of a wall of the at least one tube to a predetermined maximum thickness to minimize the effect on the radiation distribution and to substantially prevent the formation of cold zones.

22. A method according to claim 21, wherein the thickness of the wall of the at least one tube is equal to or less than 0.002 inches, and wherein the predetermined maximum thickness is less than or equal to 0.030 inches.

23. A brachytherapy source for use in radiation treatment of an affected tissue region, the brachytherapy source comprising:
   radioactive material; and
   a housing for containing the radioactive material, the housing being formed by at least one tube having two ends, wherein each of the two ends of the at least one tube are sealed by welding to permit a radiation distribution approximating a point source at each of the two ends which is substantially free of cold zones, and wherein each of the sealed ends taper from a thickness of a wall of the at least one tube to a maximum thickness.

24. A brachytherapy source according to claim 23, wherein the thickness of the wall of the at least one tube is equal to or less than 0.002 inches, and wherein the maximum thickness is less than or equal to 0.030 inches.

25. A method of manufacturing a brachytherapy source for use in radiation treatment of the body, the method comprising the steps of:
   providing radioactive material;
   forming a housing from at least one tube with an axis, the tube having two ends at opposite ends of the axis, to contain the radioactive material; and
   laser welding the two ends of the at least one tube and permit a radiation distribution of the brachytherapy source which approximates a point source that is substantially free of cold zones, the step of laser welding including:
   emitting radiation from a laser while rotating the tube about the axis relative to the laser to seal the radioactive material in the at least one tube;
   activating the laser in a first series of pulses to initially collapse one end of the at least one tube and to at least partially close off the one end;
   activating the laser for a second series of pulses to seal off the one end of the at least one tube and remove excess material;
   activating the laser in a third series of pulses to initially collapse the other end of the at least one tube and to at least partially close off the other end; and
   activating the laser for a fourth series of pulses to seal off the other end of the at least one tube and remove excess material.

26. A method of manufacturing a brachytherapy source for use in radiation treatment of an affected tissue region, the method comprising the steps of:
   providing radioactive material;
   forming a housing from at least one tube having two ends to contain the radioactive material;
   welding the two ends of the at least one tube to seal the radioactive material while permitting a radiation distribution approximating a point source at each of the two ends which is substantially free of cold zones; and
   tapering each of the two sealed ends from a thickness of a wall of the at least one tube to a predetermined maximum thickness to minimize any effects on the radiation distribution.

27. A method according to claim 26, wherein the thickness of the wall of the at least one tube is equal to or less than 0.002 inches, and wherein the predetermined maximum thickness is less than or equal to 0.030 inches.

28. A brachytherapy source for use in radiation treatment of an affected tissue region, the brachytherapy source comprising:
   radioactive material; and
   a housing for containing the radioactive material, the housing being formed by at least one tube having an axis, two ends and a substantially uniform minimum wall thickness transverse to the axis between each of the two ends, wherein each of the two ends of the at least one tube are sealed to form a wall thickness which tapers from a maximum thickness at about the axis to the minimum thickness to permit a radiation distribution approximating a point source at each of the two ends which is substantially free of cold zones.

29. A brachytherapy source according to claim 28, wherein the minimum thickness of the wall of the at least one tube is equal to or less than 0.002 inches, and wherein the maximum thickness is less than or equal to 0.030 inches.

30. A method of manufacturing a brachytherapy source for use in radiation treatment of an affected tissue region, the method comprising the steps of:

providing radioactive material;

forming a housing from at least one tube having two ends to contain the radioactive material, the housing having an axis and a substantially uniform wall thickness transverse to the axis between the two ends; and welding the two ends of the at least one tube to seal the radioactive material to form a wall thickness which tapers from a maximum wall thickness at about the axis to the minimum thickness to permit a radiation distribution approximating a point source at each of the two ends which is substantially free of cold zones.

31. A method according to claim 30, the method further including tapering the wall thickness at each end from a wall thickness at about the axis which is less than or equal to 0.030 inches to a wall thickness equal to or less than 0.002 inches.

* * * * *